(12) United States Patent
Xu et al.

(10) Patent No.: US 10,322,396 B2
(45) Date of Patent: Jun. 18, 2019

(54) CIRCULATING MAGNETOELECTRIC-INDUCTION REACTION SYSTEM AND APPLICATION THEREOF

(71) Applicant: Jiangnan University, Wuxi (CN)

(72) Inventors: Xueming Xu, Wuxi (CN); Na Yang, Wuxi (CN); Yuyi Zhou, Wuxi (CN); Yamei Jin, Wuxi (CN); Fengfeng Wu, Wuxi (CN); Yisheng Chen, Wuxi (CN); Zhengyu Jin, Wuxi (CN); Dandan Li, Wuxi (CN); Shilin Wu, Wuxi (CN); Yao Zhang, Wuxi (CN)

(73) Assignee: Jiangnam University, Wuxi (CN)

( * ) Notice: Subject to any disclaimer, the term of this patent is extended or adjusted under 35 U.S.C. 154(b) by 0 days.

(21) Appl. No.: 15/759,157

(22) PCT Filed: May 31, 2016

(86) PCT No.: PCT/CN2016/084142
§ 371 (c)(1),
(2) Date: Mar. 9, 2018

(87) PCT Pub. No.: WO2017/045434
PCT Pub. Date: Mar. 23, 2017

(65) Prior Publication Data
US 2019/0054442 A1     Feb. 21, 2019

(30) Foreign Application Priority Data
Sep. 14, 2015   (CN) .......................... 2015 1 0584007

(51) Int. Cl.
*C12M 1/42*     (2006.01)
*B01J 19/12*    (2006.01)
(Continued)

(52) U.S. Cl.
CPC ............. *B01J 19/12* (2013.01); *B01J 19/087* (2013.01); *C12M 1/00* (2013.01); *C12N 13/00* (2013.01);
(Continued)

(58) Field of Classification Search
CPC .... B01J 19/087; B01D 11/0419; C12N 13/00; C12M 23/06; C12M 27/10; C12M 29/18; C12M 35/02; C12M 35/06
See application file for complete search history.

(56) References Cited

FOREIGN PATENT DOCUMENTS

| CN | 104014290 A | 9/2014 |
|----|-------------|--------|
| CN | 104722255 A | 6/2015 |

(Continued)

OTHER PUBLICATIONS

International Search Report of international application PCT/CN2016/084142.

(Continued)

*Primary Examiner* — William H. Beisner
(74) *Attorney, Agent, or Firm* — Wang Law Firm, Inc.

(57) ABSTRACT

The present invention discloses a circulating magnetoelectric-induction reaction system and application thereof. The system comprises an alternating induction voltage unit, an alternating induction magnetic field unit, a low-frequency power supply, and a feed liquid container. The alternating induction voltage unit is mainly composed of a closed iron core, a primary coil, a secondary coil, and an induction voltage cavity. The alternating induction magnetic field unit is mainly composed of a C-shaped iron core, a primary coil, and a magnetic field cavity. The low-frequency power supply is connected to the primary coils in the alternating induction voltage unit and the alternating induction magnetic field unit and provides excitation voltage for the primary coils. The secondary coil comprises an insulating (Continued)

pipeline, which serves as a feed liquid circulating pipeline, and has both ends exposed out of the induction voltage cavity, with one end as a feed inlet and the other as a discharge outlet. The feed liquid container communicates with the feed liquid circulating pipelines in the alternating induction voltage unit and the alternating induction magnetic field unit to form a feed liquid circulation loop. Through the application, continuous-flow processing can be achieved, electrochemical reaction and ionic polarization can be avoided, and production and processing can be conducted efficiently and rapidly in a large scale.

19 Claims, 3 Drawing Sheets

(51) Int. Cl.
  *C12M 1/00* (2006.01)
  *H01F 1/057* (2006.01)
  *B01J 19/08* (2006.01)
  *C12N 13/00* (2006.01)
  *B01D 11/04* (2006.01)
  *B01D 11/02* (2006.01)

(52) U.S. Cl.
  CPC .......... *H01F 1/057* (2013.01); *B01D 11/0211* (2013.01); *B01D 11/0419* (2013.01); *C12M 29/18* (2013.01); *C12M 35/02* (2013.01); *C12M 35/06* (2013.01)

(56) References Cited

FOREIGN PATENT DOCUMENTS

| CN | 105268388 A | 1/2016 |
| EP | 2839875 A1 | 2/2015 |
| WO | 2006006946 A1 | 1/2006 |

OTHER PUBLICATIONS

Office Action of CN 201510584007.7, published on Oct. 26, 2016.
Office Action of CN 201510584007.7, published on May 16, 2017.
Notification of Patent Grant of CN 201510584007.7, published on Jul. 25, 2017.

CIRCULATING MAGNETOELECTRIC-INDUCTION REACTION SYSTEM AND APPLICATION THEREOF

TECHNICAL FIELD

The application relates to a circulating magnetoelectric-induction reaction system and application thereof, for example the application in the fields of hydrolysis and modification of natural polymers, extraction of natural compounds, and variation of reaction kinetic or terminal products.

DESCRIPTION OF RELATED ART

A biochemical reaction system is a system device that can provide appropriate reaction conditions for chemical and biological reactions and convert raw materials into specific products under certain operation parameters. The system is applied to light industries, such as chemical engineering and the food industry. Existing liquid-phase reactors include kettle reactors, hydrothermal synthesis reactors, catalytic reactors, microwave chemical reactors, electrochemical reactors, and the like. The controllable operating conditions of the aforementioned reactors include temperature, pressure, vacuum level, stirring rate, light source type, light source power, microwave power, electrode form, electrode area, voltage intensity, and the like. However, the control parameters of the reactors are simple, and thus multidimensional control over a reaction system cannot be achieved.

BRIEF SUMMARY OF THE INVENTION

The application mainly aims to provide a circulating magnetoelectric-induction reaction system and application thereof to overcoming defects in prior art.

The technical scheme adopted by the application to achieve the aforementioned purpose states the following:

A circulating magnetoelectric-induction reaction system provided by an embodiment of the application comprises
 an alternating induction voltage unit comprising:
 a closed iron core,
 a primary coil wound on one side of the closed iron core,
 a secondary coil wound on the other side of the closed iron core and arranged in an induction voltage cavity. It comprises an insulating pipeline that serves as a feed liquid circulating pipeline and has two ends exposed out of the induction voltage cavity, with one end as a feed inlet and the other as a discharge outlet. An alternating induction magnetic field unit, comprising:
 a C-shaped iron core,
 a primary coil wound on one side of the C-shaped iron core,
 a magnetic field cavity that penetrates through an opening of the C-shaped iron core and has a feed liquid circulating pipeline arranged in it;
 a low-frequency power supply connected to the primary coils in the alternating induction voltage unit, which provides excitation voltage for the primary coils;
 and a feed liquid container in which the feed liquid container communicates with the feed liquid circulating pipelines in the alternating induction voltage unit and the alternating induction magnetic field unit to form a feed liquid circulation loop.

In certain preferred embodiments, the low-frequency power supply transmits sine waves or square signals with the following parameters: frequency range, 400-700 Hz; peak voltage of the signals, 0-1000 V; output power, 0-2 kW; and duty cycle, 5%-90%.

In certain preferred embodiments, the circulating magnetoelectric-induction reaction system further comprises a temperature control unit used to control the temperature of feed liquid.

Preferably, the temperature control unit comprises a constant-temperature jacket layer arranged in the induction voltage cavity. The insulating pipeline is wrapped with the constant-temperature jacket layer, which communicates with a constant-temperature circulating bath through a constant-temperature circulating bath inlet and a constant-temperature circulating bath outlet distributed in the induction voltage cavity.

Preferably, the temperature control unit comprises a constant-temperature jacket layer arranged in the magnetic field cavity. The feed liquid circulating pipeline is wrapped with the constant-temperature jacket layer, which communicates with the constant-temperature circulating bath through a constant-temperature circulating bath inlet and a constant-temperature circulating bath outlet distributed in the magnetic field cavity.

Preferably, the temperature control unit comprises a constant-temperature bath equipped with the feed liquid container.

Preferably, at least one constant-temperature circulating bath and at least one constant-temperature jacket layer are connected in series to form a constant-temperature circulation loop.

In certain preferred embodiments, the closed iron core or the C-shaped iron core is at least made of nickel steel, and the operating frequency range of the iron cores is 400-700 Hz.

Preferably, the ratio of the number of turns of the primary coil wound on the closed iron core to the number of turns of the secondary coil wound on the closed iron core is 80-400: 25-30.

Preferably, the number of turns of the primary coil wound on the closed iron core is 80-400, and the number of turns of the secondary coil wound on the closed iron core is 25-30.

Preferably, the number of turns of the primary coil wound on the C-shaped iron core is 500-600.

Wherein, the primary coils can, at least, be made of copper.

Wherein, the insulating pipeline can comprise a glass spring.

Preferably, the inner diameter of the glass spring is 3-5 mm.

Preferably, the length of the induction voltage cavity is less than or equal to 500 mm.

Preferably, the diameter of the feed liquid circulating pipeline in the magnetic field cavity is 3-5 mm.

Preferably, the length of the magnetic field cavity is less than or equal to 300 mm.

In certain preferred embodiments, the feed liquid pipeline of the induction voltage cavity is connected to the feed liquid pipeline of the magnetic field cavity through a silicone tube.

In certain preferred embodiments, the circulating magnetoelectric-induction reaction system further comprises a device used to drive the feed liquid to flow cyclically in the feed liquid circulation loop.

Preferably, the flow rate of the feed liquid in the feed liquid circulation loop is 50 μL/s-500 mL/s.

In certain embodiments, the feed liquid container is connected to the feed liquid circulating pipelines in the alternating induction voltage unit and the alternating induction magnetic field unit to form a feed liquid circulation loop.

Preferably, the temperature of the feed liquid in the feed liquid circulation loop is −20° C.-130° C.

The embodiment of the application further provides for the use of the circulating magnetoelectric-induction reaction system in hydrolysis and modification of natural polymers, extraction of natural compounds, and the variation of reaction kinetic or terminal products.

Compared with the prior art, the circulating magnetoelectric-induction reaction system of the application has the following advantages:

1. The circulating magnetoelectric-induction reaction system of the application provides more operating conditions, including the induction voltage excitation signal intensity, induction voltage excitation signal type, induction voltage excitation signal frequency, alternating magnetic field excitation signal intensity, alternating magnetic field excitation signal type, alternating magnetic field excitation signal frequency, temperature, and flow rate of a solution. Furthermore, an alternating electric field in the reaction solution comes from induction voltage so that no electrified electrode is adopted by the device, electrochemical reaction, and ionic polarization on the surface of electrode is avoided accordingly.

2. The circulating magnetoelectric-induction reaction system of the application creates a special mass transfer effect on charged ions, charged compounds, charged particles, and charged protein or enzymes with different charge-to-mass ratios in a solution system by means of fluid hydrodynamic force, alternating electric field force, and alternating magnetic field force. Thus, the chemical reaction kinetic or terminal products are effectively influenced and changed.

3. The circulating magnetoelectric-induction reaction system of the application is easy and convenient to operate, and improves reaction efficiency.

DESCRIPTION OF MARKS IN THE DRAWINGS

Figure 1:
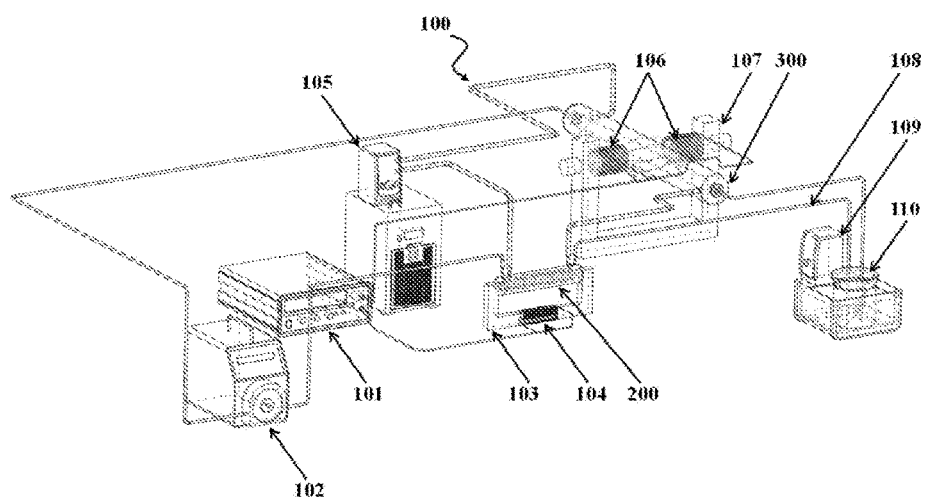
FIG. 1 is a structure diagram of a circulating magnetoelectric-induction reaction system in one typical embodiment of the application.

Processing device chain 100, low-frequency power supply 101, peristaltic pump 102, O-shaped nickel-steel iron core 103, induction voltage primary coil 104, constant-temperature circulating bath 105, alternating magnetic field primary coil 106, C-shaped nickel-steel iron core 107, silicone tube 108, constant-temperature bath 109, reaction solution container 110, induction voltage cavity 200, glass spring 201, electric field constant-temperature jacket layer 202, feed liquid inlet 203, feed liquid outlet 204, constant-temperature circulating bath inlet 205, constant-temperature circulating bath outlet 206, magnetic field cavity 300, magnetic field constant-temperature jacket layer 301, magnetic field constant-temperature jacket layer feed inlet 302, magnetic field constant-temperature jacket layer discharge outlet 303, constant-temperature circulating bath inlet 304, constant-temperature circulating bath outlet 305.

DETAILED DESCRIPTION OF THE INVENTION

To overcome the defects in the prior art, the inventors present the technical scheme of the application through a long-term study and much practice. Further explanation of the technical scheme, implementation process, principle, and the like of the technical scheme is presented as follows:

On one aspect, the application relates to a circulating magnetoelectric-induction reaction system, which comprises:

an alternating induction voltage unit comprising
a closed iron core;
a primary coil wound on one side of the closed iron core;
a secondary coil in which the secondary coil is wound on the other side of the closed iron core and arranged in an induction voltage cavity and comprises an insulating pipeline, which serves as a feed liquid circulating pipeline, and with its two ends exposed out of the induction voltage cavity and used as a feed inlet and a discharge outlet;
an alternating induction magnetic field unit comprising:
a C-shaped iron core,
a primary coil wound on one side of the C-shaped iron core,
a magnetic field cavity that penetrates through an opening of the C-shaped iron core and in which a feed liquid circulating pipeline is arranged;
a low-frequency power supply connected to the primary coils in the alternating induction voltage unit and the alternating induction magnetic field unit and provides excitation voltage for the primary coils;
and a feed liquid container, which communicates with the feed liquid circulating pipelines in the alternating induction voltage unit and the alternating induction magnetic field unit to form a feed liquid circulation loop.

FIG. 1 shows a structure diagram of a circulating magnetoelectric-induction reaction system in one typical embodiment of the application, mainly composed of a low-frequency power supply, primary coils, iron cores, induction voltage cavity, a magnetic field cavity, a silicone tube, a peristaltic pump, a temperature control unit, and the like.

When the circulating magnetoelectric-induction reaction system of the application operates, a flowing reaction solution (feed liquid) serves as a conductor of the primary coils and is supported by an insulating pipeline (for example, a glass spring). The primary coils are excited by the low-frequency power supply, and alternating magnetic fluxes are generated in the iron cores. An alternating induction voltage is also generated in the loop system, with the reaction solution serving as the conductor of the loop accordingly. Meanwhile, a generated magnetic field affects the reaction solution flowing in the magnetic field cavity. Charged ions, charged particles, charged organic compounds, or charged proteins and enzymes, which move in the reaction system, are affected by the induction voltage, namely, the magnetic field force and the alternating magnetic field, jointly referred to as the Lorentz force. Finally, the biochemical reaction rate or terminal products change.

More specifically, the principle of the circulating magnetoelectric-induction reaction system of the application mainly lies in the following:

Transformers are electric energy-magnetic energy-electric energy conversion equipment. By applying alternating excitation voltage $U_p$ to a primary coil ($N_p$) of a single-phase transformer, the magnetic flux changes correspondingly in an iron core. As shown in Formula (1), the numerical value of the magnetic flux is directly proportional to the number of turns of the coil:

$$U_p = -N_p \frac{d\phi}{dt} \tag{1}$$

In the formula, $U_p$=excitation voltage, $N_p$=the number of turns of the primary coil, $d\Phi$=magnetic flux differential, dt=time differential.

The electromagnetic induction principle is based on Ampere's circuital law, which states that in a magnetic field area, the integral of any closed line in the selected magnetic field H is equal to the algebraic sum of conductive current in the surface defined by the closed line penetrating through a closed path, as represented in Formula (2) and Formula (3):

$$\oint \vec{H} \cdot \vec{dl} = i \tag{2}$$

$$\sum_N H \cdot l = Ni \tag{3}$$

In the formula, H=magnetic field intensity, l=the length of a closed magnetic circuit, i=current in the closed path, N=the number of turns of the coil.

The changing magnetic flux in the magnetic circuit of the iron core generates induction voltage $E_s$ in a secondary coil ($N_s$):

$$E_s = -N_s \frac{d\phi}{dt} \tag{4}$$

In the formula, $E_s$=induction voltage, $N_s$=the number of turns of the secondary coil, $d\Phi$=magnetic flux differential, dt=time differential.

The relation of all parameters is shown in Formula (5), as follows:

$$E_p/E_s = U_p/U_s = N_p/N_s \tag{5}$$

E is the induction voltage, U is the terminal voltage, and N is the number of turns of the coils. While the excitation voltage and the ratio of the number of turns of the primary coil to the number of turns of the secondary coil are fixed, the induction voltage is a fixed value. Since internal impedance exists in the secondary coil, the induction voltage $E_s$ in a secondary circuit is shared by an external load and coil impedance. If a conductive solution containing a large quantity of charged ions, charged compounds, charged particles, and protein and enzymes with the surfaces charged is used as a conductor of the secondary coil, then under the influence of the alternating magnetic flux, induction voltage still exists in the solution according to the ampere circuit law.

The biochemical solution system contains a certain quantity of charged ions, charged compounds, charged particles, and protein and enzymes with the surfaces charged, and these charged species move directionally under the influence of fluid hydrodynamic force. Meanwhile, the charged species also move relatively under the influence of an electric field; that is, positively-charged species move toward the cathode, whereas negatively-charged species move toward the anode. The charged species can also be affected by a magnetic field—that is, the Lorentz force—when making a cutting magnetic movement, causing a deviation in the movement tracks.

Generally, the chemical reaction rate in the solution system is closely related to the activation energy, which can be reduced if the temperature is increased. The lower the activation energy, the higher the reaction rate is. When the reaction solution is not affected by the fluid hydrodynamic force, alternating induction voltage, and alternating magnetic field, the charged solutes in the solution system exhibit an irregular thermodynamic movement. However, when the flowing reaction solution is affected by the induction voltage and alternating magnetic field, then charged ions, charged compounds, charged particles, charged protein and enzymes, and other solutes in the reaction solution can move directionally in a large scale, affecting the chemical reaction kinetic or terminal products.

In certain embodiments, the low-frequency power supply transmits sine waves or square waves with the following parameters: frequency range, 400-700 Hz; peak voltage of the signals, 0-1000 V; output power, 0-2 kW, and duty cycle of the square waves, 5%-90%. In this manner, the primary coils on the closed iron core and C-shaped iron core are simultaneously excited to obtain an alternating induction voltage and an alternating magnetic field.

In certain embodiments, the iron cores are made of nickel-steel materials, and the operating frequency of the iron cores is 400-700 Hz; one iron core is used for generating alternating induction voltage and exhibits a closed O shape, and the other iron core is used for generating the alternating magnetic field and exhibits a non-closed C shape.

In certain embodiments, the primary coils are copper coils; the number of turns of the primary coil wound on the O-shaped iron core is 80-400, and the number of turns of the primary coil wound on the C-shaped iron core is 500-600.

In certain embodiments, a glass spring is arranged in the induction voltage cavity. A feed inlet and a discharge outlet for leading the reaction solution out from the two sides are formed in the glass spring, which also supports the reaction solution serving as a conductor of the secondary coil and is wound on one side of the O-shaped nickel-steel iron core. The inner diameter of the glass spring is 3-5 mm, and the number of turns of the glass spring is 25-30. A constant-temperature jacket layer is arranged outside the glass spring. A constant-temperature circulating bath inlet and a constant-temperature circulating bath outlet, which are formed on the two sides of the glass induction voltage cavity, are used for guiding in fluid at controlled temperatures to maintain the temperature of the reaction solution in the glass spring.

Preferably, the length of the induction voltage cavity is not over 500 mm.

Preferably, the induction voltage cavity can be a glass induction voltage cavity.

In certain embodiments, the reaction solution directly circulates in the magnetic field cavity (e.g., a glass magnetic field cavity). The inner diameter of the circulating pipeline is preferably 3-5 mm. In addition, a constant-temperature jacket layer is arranged outside the reaction solution circulating pipeline. A constant-temperature circulating bath inlet and a constant-temperature circulating bath outlet are formed on the two sides of the glass magnetic field cavity and used for guiding in fluid at controlled temperatures to maintain the temperature of the reaction solution in the circulating pipeline. The glass magnetic field cavity, preferably not exceeding 300 mm, directly penetrates through the magnetic field area of the C-shaped iron core. Thus, the flowing reaction solution can be affected by the alternating magnetic field.

In certain embodiments, a corrosion-resistant and high-temperature-resistant silicone tube is used as a pipeline for connecting the glass induction cavity and the glass magnetic field cavity. The peristaltic pump is arranged on the silicone tube for the reaction solution to circulate cyclically. The flow rate is 50 μL/s-300 mL/s.

In certain embodiments, the reaction solution container is placed in the constant-temperature bath and is maintained at a required temperature.

In certain embodiments, the temperature control unit comprises a constant-temperature circulating bath and a constant-temperature bath. The constant-temperature circulating bath communicates with the constant-temperature circulating bath inlets and the constant-temperature circulating bath outlets on the constant-temperature jacket layers in the glass induction voltage cavity and the glass magnetic field cavity. The temperature of feed liquid is kept within the range of −20° C.-130° C.

In the typical embodiment shown in FIG. 1, the operation of the circulating magnetoelectric-induction reaction system includes the steps in starting the peristaltic pump for the feed liquid to flow cyclically. The temperature of the feed liquid in a feed liquid circulating system then changes through a constant-temperature circulating system. Subsequently, the induction voltage primary coil and the alternating magnetic field primary coil are excited through the control unit. Thus, the feed liquid is processed in the induction voltage cavity and the magnetic field cavity.

The application further relates to the application of the circulating magnetoelectric-induction reaction system, such as the application for the hydrolysis and the modification of natural polymers, enhanced extraction of natural products, and the variation of reaction kinetic or terminal products. According to the application, the peculiar mass transfer effect of charged ions, charged compounds, charged particles, and charged protein or enzymes with different charge-to-mass ratios in a solution system is created mainly by means of fluid hydrodynamic force, alternating electric field force, and alternating magnetic field force. The chemical reaction kinetic or terminal products are effectively influenced and changed.

Compared with the prior art, the circulating magnetoelectric-induction reaction system of the application provides more operating conditions, including the induction voltage excitation signal intensity, induction voltage excitation signal type, induction voltage excitation signal frequency, alternating magnetic field excitation signal intensity, alternating magnetic field excitation signal type, alternating magnetic field excitation signal frequency, temperature, and flow rate of a solution. Moreover, the alternating electric field in the reaction solution comes from the induction voltage so that no electrified pole plate or electrode is adopted by the device, and electrochemical reaction and ionic polarization on the surface of the pole plate or the electrode are avoided accordingly.

A more specific explanation of the technical scheme of the application is presented with several embodiments, as follows:

First Embodiment: Application on the Hydrolysis

With the preparation of reducing sugar through acid hydrolysis of bagasse cellulose as an example, a further description of the application of the circulating magneto-electric-induction reaction system in the hydrolysis reaction of natural polymer raw materials is presented, as follows.

Figure 2:
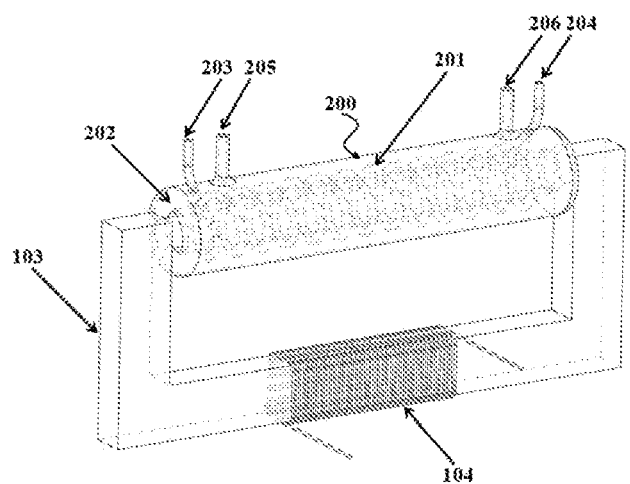
FIG. 2 is a structure diagram of an induction voltage cavity of the circulating magnetoelectric-induction reaction system in one typical embodiment of the application.
Figure 3:
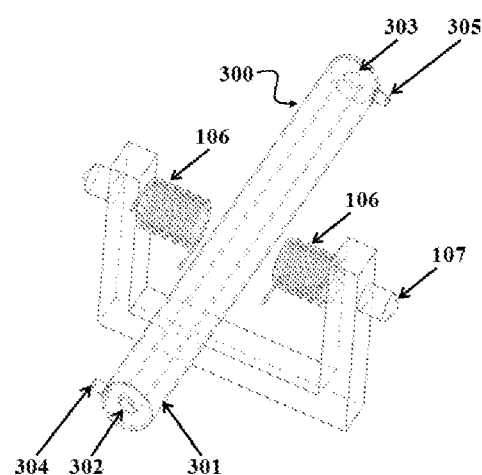
FIG. 3 is a structure diagram of a magnetic field cavity of the circulating magnetoelectric-induction reaction system in one typical embodiment of the application.

As shown in FIGS. 1-3, in the embodiment, a circulating magnetoelectric-induction reaction system is provided by the application and comprises a processing device chain 100, an induction voltage cavity 200, and a magnetic field cavity 300.

As shown in FIG. 1, the reaction system chain 100 comprises a low-frequency power supply 101, a peristaltic pump 102, an O-shaped nickel-steel iron core 103, an induction voltage primary coil 104, an induction voltage cavity 200, a constant-temperature circulating bath 105, an alternating magnetic field primary coil 106, a C-shaped nickel-steel iron core 107, a magnetic field cavity 300, a corrosion-resistant and high-temperature-resistant silicone tube 108, a constant-temperature bath 109, and a reaction solution container 110. Two output terminals of the low-frequency power supply 101 are connected to the induction voltage primary coil 104 and alternating magnetic field primary coil 106. The low-frequency power supply 101 transmits sine waves and pulse waves with a frequency of 400 Hz-700 Hz, voltage of 0-1000 V, output power of 0-2 kW, and duty cycle of the pulse waves is 5%-90%. The number of turns of the induction voltage primary coil 104 is 80-400, and the induction voltage primary coil 104 is wound on one side of the O-shaped nickel-steel iron core 103. The operating frequency range of the O-shaped nickel-steel iron core 103 is 400 Hz-700 Hz, the rated power of the O-shaped nickel-steel iron core 103 is 2 kW, the central perimeter of the iron core is 850 mm, and the thickness of the iron core is 20 mm. Meanwhile, the number of turns of the alternating magnetic field primary coil 106 is 500-600, and the alternating magnetic field primary coil 106 is wound on one side of the C-shaped nickel-steel iron core 107. The operating frequency range of the C-shaped nickel-steel iron core 107 is 400 Hz-700 Hz, the rated power of the C-shaped nickel-steel iron core 107 is 2 kW, the central perimeter of the iron core is 800 mm, and the thickness of the iron core is 20 mm. The other side of the O-shaped nickel-steel iron core 103 penetrates the induction voltage cavity 200, ensuring that the glass spring 201 in the induction voltage cavity 200 is wound on the O-shaped nickel-steel iron core 103, the number of turns of the glass spring 201 is 25-30, and the inner diameter of the glass spring is 4 mm. FIG. 2 shows that the induction voltage cavity 200 includes the glass spring 201, a constant-temperature jacket layer 202, a feed inlet 203, a discharge outlet 204, a constant-temperature circulating bath inlet 205, and a constant-temperature circulating bath outlet 206. The two ends of the glass spring 201 are exposed out of two corresponding ends of the induction voltage cavity 200 to serve as the feed inlet 203 and the discharge outlet 204 for feed liquid. The electric field constant-temperature jacket layer 202 is located outside the glass spring 201. The constant-temperature circulating bath inlet 205 and the constant-temperature circulating bath outlet 206 are arranged at the two ends of the induction voltage cavity 200. The inlet and outlet are used for guiding in fluid at controlled temperatures to maintain the temperature of the circulating solution in the glass spring 201. The length of the induction voltage cavity is 500 mm.

As shown in FIG. 3, the magnetic field cavity 300 includes a magnetic field constant-temperature jacket layer 301, a magnetic field constant-temperature jacket layer feed inlet 302, a magnetic field constant-temperature jacket layer discharge outlet 303, a constant-temperature circulating bath inlet 304, and a constant-temperature circulating bath outlet 305. The reaction solution flows in from the magnetic field constant-temperature jacket layer feed inlet 302 and then flows out from the magnetic field constant-temperature jacket layer discharge outlet 303. The constant-temperature circulating bath inlet 304 and the constant-temperature circulating bath outlet 305 are arranged on the magnetic field constant-temperature jacket layer 301, located at the two ends of the magnetic field cavity 300. The inlet and outlet are used for guiding in fluid at controlled temperatures to maintain the temperature of the circulating solution in the pipeline. The length of the magnetic field cavity 300 is 200 mm. The alternating magnetic field primary coil 106 on the C-shaped nickel-steel iron core 107 is excited by alternating voltage; thus, an alternating magnetic field is generated at the open end of the C-shaped nickel-steel iron core 107. The magnetic field cavity 300 directly penetrates the alternating magnetic field area. The reaction solution is driven by fluid hydrodynamic force to produce a cutting magnetic movement.

The induction voltage cavity 200, magnetic field cavity 300, and reaction solution container 110 are connected through the corrosion-resistant and high-temperature-resistant silicone tube 108 and form a series loop. The peristaltic pump 102 is arranged in the silicone tube 108 for the reaction solution to flow cyclically—that is, the volume flow rate of the solution under the effect of fluid hydrodynamic force is 50 μL-300 mL, and the reaction solution container 110 needs to be placed in the constant-temperature bath 109 at the required temperature.

The constant-temperature circulating bath 105 is connected to the electric field constant-temperature jacket layer 202 and the magnetic field constant-temperature jacket layer 301. The temperature in the container is kept within the range of −20° C.-130° C.; that is, the constant-temperature circulating bath outlet 206 in the induction voltage cavity 200 is connected to the constant-temperature circulating bath inlet 304 in the magnetic field cavity 300.

Efficient acid hydrolysis reaction of bagasse cellulose through the method comprises the following steps:

Step 1: 1000 g of crushed dry 80-mesh bagasse powder is placed in a 15 L plastic cup 110. Distilled water amounting to 10 L is added, and the feed liquid is evenly mixed and stirred for 40 min in the constant-temperature bath 109 at 60° C., to be preheated, and 1 L of hydrochloric acid solution with a concentration of 6.7% is added gradually added at the same time. The feed liquid is again stirred for 5 min and then evenly mixed;

Step 2: The peristaltic pump 102 is started to ensure that the feed liquid passes through the glass spring 201 of the induction voltage cavity 200 and the magnetic field cavity 300 and starts to flow cyclically at the volume flow rate of 80 mL/s. The constant-temperature circulating bath 105 is then started at 60° C.;

Step 3: The low-frequency power supply 101 is started to excite the induction voltage primary coil 104 and the alternating magnetic field primary coil 106. Sine waves are selected, with a frequency of 400 Hz, voltage amplitude of 500 V, and rated power of 2 kW. The number of turns of the induction voltage primary coil 104 is 200, and that of the alternating magnetic field primary coil 106 is 500. The impedance $Z_1$ of the induction voltage primary coil 104 is 404Ω, and the impedance $Z_2$ of the alternating magnetic field primary coil 106 is 704Ω to obtain the following parameters: current $I_1$ of the induction voltage primary coil 104, 1.24 A; current $I_2$ of the alternating magnetic field primary coil 106, 0.71 A; circuit power $P_1$ of the induction voltage primary coil 104, 620 W; circuit power $P_2$ of the alternating magnetic field primary coil 106, 355 W; number of turns of the glass spring 201, 25; number of turns of the secondary coil, 25; and turn ratio, 8:1. According to the voltage distribution principle of the transformer, the induction voltage of the feed liquid in the glass spring 201 is 62.5 V. Detected using a teslameter, the alternating magnetic field at the opening of the C-shaped nickel-steel iron core 107 is 940 Gs, and $P_1+P_2=620$ W+355 W=975 W<the rated power 2000 W; that is, the low-frequency power supply enables the system to operate normally.

Step 4: Cyclic processing is conducted for 7 h and then stopped. The feed liquid is discharged, the $NaHCO_3$ solution with a mass fraction of 1% is added instantly when the feed liquid reaches room temperature, the pH of the feed liquid is adjusted to 7, and the reaction is ended. The feed liquid is then centrifuged at the rotating speed of 5000 rpm for 20 min to remove sediment.

The content of the reducing sugar in the coarse bagasse hydrolysate obtained through the circulating magnetoelectric-induction reaction system reaches 21.45%; however, the content is only 6.59% when no low-frequency excitation voltage is applied to the induction voltage primary coil 104 and the alternating magnetic field primary coil 106.

Second Embodiment: Esterification of Ethyl Alcohol-Lactic Acid

The application of the system is further described with the application of the circulating magnetoelectric-induction reaction system in the first embodiment to change the reaction kinetic as an example. The application of the system comprises the following steps:

Step 1: 5000 mL of a lactic acid aqueous solution with a concentration of 10 mol/L and 5600 mL of an aqueous solution of ethyl alcohol, with a concentration of 10 mol/L, are mixed and stirred for 20 min in the constant-temperature bath 109 at 25° C., to be preheated;

Step 2: The peristaltic pump 102 is started to ensure that the feed liquid passes through the glass spring 201 of the induction voltage cavity 200 and the magnetic field cavity 300 and starts to flow cyclically at the volume flow rate of 80 μL/s. The constant-temperature circulating bath 105 is then started at 40° C.;

Step 3: The low-frequency power supply 101 is started to excite the induction voltage primary coil 104 and the alternating magnetic field primary coil 106. Sine waves are selected. The frequency is 700 Hz, the voltage amplitude is 900 V, and the rated power is 2 kW. The number of turns of the induction voltage primary coil 104 is 400, and the number of turns of the alternating magnetic field primary coil 106 is 600. The impedance of the coils is detected through an impedance analyzer when the frequency is 700 Hz; specifically, the impedance $Z_1$ of the induction voltage primary coil 104 is 702Ω, and the impedance $Z_2$ of the alternating magnetic field primary coil 106 is 1001Ω to obtain the following parameters: current $I_1$ of the induction voltage primary coil 104, 1.28 A; current $I_2$ of the alternating magnetic field primary coil 106, 0.89 A; circuit power $P_1$ of the induction voltage primary coil 104, 1152 W; circuit power $P_2$ of the alternating magnetic field primary coil 106, 801 W; and number of turns of the glass spring 201, 20; that is, the number of turns of the secondary coil is 20, and the turn ratio is 20:1. According to the voltage distribution principle of the transformer, the induction voltage of the feed liquid in the glass spring 201 is 45 V. Detected through a teslameter, the alternating magnetic field at the opening of the C-shaped nickel-steel iron core 107 is 1284 Gs, and $P_1+P_2=1152$ W+801 W=1953 W<the rated power 2000 W; that is, the low-frequency power supply enables the system to operate normally.

Step 4: Cyclic processing is conducted for 10 h and then stopped. The feed liquid is discharged, and the ethyl lactate concentration is analyzed after the feed liquid reaches room temperature.

The concentration of the ethyl lactate in the solution obtained through the circulating magnetoelectric-induction reaction system reaches 0.25 mol/L; the concentration is only 0.05 mol/L when no low-frequency excitation voltage is applied to the induction voltage primary coil 104 and the alternating magnetic field primary coil 106.

Third Embodiment: Efficient Extraction of Soluble Fishbone Calcium

The method is further described with the application of the circulating magnetoelectric-induction reaction system in the first embodiment in the extraction of natural products such as soluble fishbone calcium. The method consists of the following steps:

Step 1: 1200 g of crushed 120-mesh fishbone powder poured into a 15 L plastic cup 110 and added with 12 L of distilled water. The feed liquid is evenly mixed and stirred for 30 min in the constant-temperature bath 109 at 55° C. to be preheated. 1 L of the hydrochloric acid solution with a concentration of 7.8% is gradually added, and the feed liquid is again stirred for 5 min and then evenly mixed;

Step 2: The peristaltic pump 102 is started to ensure that the feed liquid passes through the glass spring 201 of the induction voltage cavity 200 and the magnetic field cavity 300 and flows cyclically at the volume flow rate of 50 mL/s. The constant-temperature circulating bath 105 is started at 55° C.;

Step 3: The low-frequency power supply 101 is started to excite the induction voltage primary coil 104 and the alternating magnetic field primary coil 106. Pulse waves are selected, with a duty ratio of 45%, frequency of 500 Hz, voltage amplitude of 800 V, and rated power of 2 kW. The number of turns of the induction voltage primary coil 104 is 300, and the number of turns of the alternating magnetic field primary coil 106 is 500. The impedance of the coils is detected using an impedance analyzer when the frequency is 500 Hz. Specifically, the impedance $Z_1$ of the induction voltage primary coil 104 is 554Ω, and the impedance $Z_2$ of the alternating magnetic field primary coil 106 is 801Ω, thus obtaining the following parameters: current $I_1$ of the induction voltage primary coil 104, 1.44 A; current $I_2$ of the alternating magnetic field primary coil 106, 0.99 A; circuit power $P_1$ of the induction voltage primary coil 104, 1152 W; circuit power $P_2$ of the alternating magnetic field primary coil 106, 792 W; number of turns of the glass spring 201, 25. The number of turns of the secondary coil is 25, and the turn ratio is 12:1. According to the voltage distribution principle of the transformer, the induction voltage of the feed liquid in the glass spring 201 is 66.7 V. Detected through a teslameter, the alternating magnetic field at the opening of the C-shaped nickel-steel iron core 107 is 1137 Gs, and $P_1+P_2=1152$ W+792 W=1944 W<the rated power 2000 V; that is, the low-frequency power supply enables the system to operate normally.

Step 4: Cyclic processing is conducted for 6 h and then stopped. The feed liquid is discharged, and the NaOH solution with the mass fraction of 1% is added instantly after the feed liquid reaches room temperature. The pH of the feed liquid is adjusted to 7, and the reaction is ended. Subsequently, the feed liquid is centrifuged at a rotating speed of 5000 rpm for 20 min to remove the sediment and thus obtain fishbone hydrolysate containing soluble calcium. Milk-white coarse calcium powder is obtained after the residual solution is dried for 48 h in an oven at 55° C.

The quantity of the coarse calcium powder obtained through the circulating magnetoelectric-induction reaction system reaches 171.74 g; by contrast, the value is only 41.74 g when no low-frequency excitation voltage is applied to the induction voltage primary coil 104 and the alternating magnetic field primary coil 106.

Fourth Embodiment: Preparation of Porous Rice Starch

The method is further described with the application of the circulating magnetoelectric-induction reaction system in the first embodiment in the modification of natural polymer compounds, such as porous rice starch. The method consists of the following steps:

Step 1: 500 g of rice starch is poured into a 15 L plastic cup and then added with 12 L of distilled water. The feed liquid is evenly mixed, obtaining a starch suspension. The hydrochloric acid solution with the concentration of 10.7% is added, the pH of the starch suspension is regulated to 3.5, and the starch suspension is preheated and stirred for 25 min at 40° C.;

Step 2: The peristaltic pump 102 is started to ensure that the feed liquid passes through the glass spring 201 of the induction voltage cavity 200 and the magnetic field cavity 300 and flows cyclically at the volume flow rate of 220 mL/s. The constant-temperature circulating bath 105 is then started at 63° C.;

Step 3: The low-frequency power supply 101 is started to excite the induction voltage primary coil 104 and the alternating magnetic field primary coil 106. Pulse waves are selected, with the duty ratio of 25%, frequency of 600 Hz, voltage amplitude of 800 V, and rated power of 2 kW. The number of turns of the induction voltage primary coil 104 is 300, and the number of turns of the alternating magnetic field primary coil 106 is 500. The impedance of the coils is detected using an impedance analyzer when the frequency is 600 Hz. Specifically, the impedance $Z_1$ of the induction voltage primary coil 104 is 611Ω, and the impedance $Z_2$ of the alternating magnetic field primary coil 106 is 933Ω, thus obtaining the following parameters: current $I_1$ of the induction voltage primary coil 104, 1.31 A; current $I_2$ of the alternating magnetic field primary coil 106, 0.86 A; circuit power $P_1$ of the induction voltage primary coil 104, 1048 W; circuit power $P_2$ of the alternating magnetic field primary coil 106, 688 W; and number of turns of the glass spring 201, 30—that is, the number of turns of the secondary coil is 30, and the turn ratio is 10:1. According to the voltage distribution principle of the transformer, the induction voltage of the feed liquid in the glass spring 201 is 80 V. Detected using a teslameter, the alternating magnetic field at the opening of the C-shaped nickel-steel iron core 107 is 1137 Gs, and $P_1+P_2=1048$ W+688 W=1736 W<the rated power 2000 W; that is, the low-frequency power supply allows the system to operate normally.

Step 4: Cyclic processing is conducted for 5 h and then stopped. The feed liquid is discharged, the NaOH solution with a mass fraction of 2% is added instantly after the feed liquid reaches room temperature, the pH of the feed liquid is adjusted to 7, and the reaction is ended. Subsequently, the feed liquid is centrifuged at a rotating speed of 3000 rpm for 15 min to remove the sediment. Modified porous rice starch is obtained after the sediment is dried for 3 h in an oven at 55° C.

The oil absorption rate of the porous rice starch, obtained by the circulating magnetoelectric-induction reaction system, reaches 114.3%. The rate is only 37.1% when no low-frequency excitation voltage is applied to the induction voltage primary coil 104 and the alternating magnetic field primary coil 106.

Notably, for a convenient and clear auxiliary illustration of the embodiments of the application, the drawings of the embodiments exhibit an extremely simplified form and adopt non-precise rates.

The use of the aforementioned embodiments is limited to illustrating the technical concept and characteristics of the application and is aimed at making those familiar with the technique understand the content and implement the application according to the content. However, the scope of protection for the application is not limited by the aforementioned embodiments. All equivalent changes or modifications made according to the essence of the application are within the protection scope of the application.

The invention claimed is:

1. A circulating magnetoelectric-induction reaction system, comprising:
   an induction voltage unit, comprising:
   a closed iron core,
   a primary coil wound on one side of the closed iron core, and
   a secondary coil wound on an opposite side of the closed iron core and arranged in an induction voltage cavity, wherein the secondary coil comprises an insulating pipeline, which is capable of being used as a feed liquid circulating pipeline, wherein the two ends of the insulating pipeline expose out of the induction voltage cavity and are used as a feed inlet and a discharge outlet, respectively;
   a magnetic field unit, comprising:
   a C-shaped iron core having three closed sides and one open side,
   a primary coil wound on two ends of the open side of the C-shaped iron core, and
   a magnetic field cavity that passes through the open side of the C-shaped iron core between the primary coil of the magnetic field unit and contains a feed liquid circulating pipeline;
   a low-frequency power supply connected to the primary coils in the induction voltage unit and the magnetic field unit, which provides an excitation voltage for the primary coils;
   a feed liquid container that communicates with the feed liquid circulating pipelines in the induction voltage unit and the magnetic field unit to form a feed liquid circulation loop;
   and a temperature control unit, which is used to adjust the temperature of feed liquid, comprising:
   a thermostatic jacket layer arranged inside the induction voltage cavity, wherein the thermostatic jacket layer wraps around the insulating pipeline and communicates with a thermostatic circulating bath through an electric field thermostatic circulating bath inlet and an electric filed thermostatic circulating bath outlet distributed in the induction voltage cavity, and
   a thermostatic jacket layer arranged inside the magnetic field cavity, wherein the thermostatic jacket layer wraps around the feed liquid circulating pipeline and communicates with the thermostatic circulating bath through a magnetic field thermostatic circulating bath inlet and a magnetic field thermostatic circulating bath outlet distributed in the magnetic field cavity.

2. The circulating magnetoelectric-induction reaction system, according to claim 1, wherein the low-frequency power supply is capable of transmitting sine wave or square wave signals in a frequency range of 400-700 Hz; wherein peak voltage of the signals is in the range of 0-1000 V; output power is in the range of 0-2 kW; and duty cycle of square waves is in the range of 5%-90%.

3. The circulating magnetoelectric-induction reaction system according to claim 1, wherein the temperature control unit comprises a thermostatic bath and the feed liquid container is positioned inside the thermostatic bath.

4. The circulating magnetoelectric-induction reaction system according to claim 1, wherein at least one thermostatic circulating bath and at least one thermostatic jacket layer connected in series to form a thermostatic circulation loop.

5. The circulating magnetoelectric induction reaction system according to claim 1, wherein the closed iron core or the C-shaped iron core comprises at least nickel steel with an operating frequency range of 400-700 Hz.

6. The circulating magnetoelectric-induction reaction system according to claim 1, wherein the ratio of the number of turns wound on the closed iron core of the primary coil compared to the number of turns of the secondary coil is 80-400:25-30.

7. The circulating magnetoelectric-induction reaction system according to claim 6, wherein the number of turns of the primary coil wound on the closed iron core is 80-400, and the number of turns of the secondary coil wound on the closed iron core is 25-30.

8. The circulating magnetoelectric-induction reaction system according to claim 1, wherein the number of turns of the primary coil wound on the C-shaped iron core is 500-600.

9. The circulating magnetoelectric-induction reaction system according to claim 1, wherein the primary coil of the induction voltage unit and the primary coil of the magnetic field unit at least can be made of copper.

10. The circulating magnetoelectric-induction reaction system according to claim 1, wherein the insulating pipeline comprises a glass spiral tube.

11. The circulating magnetoelectric-induction reaction system according to claim 10, wherein an inner diameter of the glass spiral tube is 3-5 mm.

12. The circulating magnetoelectric-induction reaction system according to claim 1, wherein the length of the induction voltage cavity is less than or equal to 500 mm.

13. The circulating magnetoelectric-induction reaction system according to claim 1, wherein the diameter of the feed liquid circulating pipeline in the magnetic field cavity is 3-5 mm.

14. The circulating magnetoelectric-induction reaction system according to claim 1, wherein the length of the magnetic field cavity is less than or equal to 300 mm.

15. The circulating magnetoelectric-induction reaction system according to claim 1, wherein the feed liquid pipeline of the induction voltage cavity is connected to the feed liquid pipeline of the magnetic field cavity through a tube.

16. The circulating magnetoelectric-induction reaction system according to claim 1, further comprises a pump used for driving the feed liquid to flow cyclically in the circulation loop.

17. The circulating magnetoelectric-induction reaction system according to claim 16, wherein the flow rate of the feed liquid in the circulation loop is 50 µL/s-500 mL/s.

18. The circulating magnetoelectric-induction reaction system according to claim 1, wherein the temperature of feed liquid in the circulation loop is −20° C.-130° C.

19. The circulating magnetoelectric-induction reaction system according to claim 1, wherein the system is used in hydrolysis and modification of natural polymers, extraction of natural compounds, and the change of reaction kinetic or final products.

* * * * *